United States Patent [19]

Gaylord et al.

[11] Patent Number: 4,849,229

[45] Date of Patent: * Jul. 18, 1989

[54] CONTROLLED RELEASE SOLID DRUG DOSAGE FORMS BASED ON MIXTURES OF WATER SOLUBLE NONIONIC CELLULOSE ETHERS AND ANIONIC SURFACTANTS

[75] Inventors: Norman G. Gaylord, New Providence, N.J.; Joseph M. Schor, Locust Valley, N.Y.

[73] Assignee: Forest Laboratories, Inc., New York, N.Y.

[*] Notice: The portion of the term of this patent subsequent to Jan. 3, 2006 has been disclaimed.

[21] Appl. No.: 141,474

[22] Filed: Jan. 5, 1988

Related U.S. Application Data

[63] Continuation-in-part of Ser. No. 592,570, Mar. 26, 1984, Pat. No. 4,795,327.

[51] Int. Cl.⁴ ................................................ A61K 9/22

[52] U.S. Cl. .................................... 424/468; 424/465; 424/494

[58] Field of Search ....................... 424/465, 468, 494

[56] References Cited

U.S. PATENT DOCUMENTS 4,259,314  3/1981  Lowey ................................... 424/19
4,404,183  9/1983  Kawata et al. ...................... 424/494

OTHER PUBLICATIONS

Daly et al, Chemical Abst. 100:144916j (1984).

Primary Examiner—Leonard Schenkman
Attorney, Agent, or Firm—Jacobs & Jacobs

[57] ABSTRACT

A therapeutically active solid unit dosage form having a controlled and prolonged release pattern upon administration, comprising a mixture of a high viscosity grade methylcellulose or hydroxypropylmethylcellulose, an alkali metal sulfate or sulfonate and a therapeutically active medicament.

5 Claims, No Drawings

CONTROLLED RELEASE SOLID DRUG DOSAGE FORMS BASED ON MIXTURES OF WATER SOLUBLE NONIONIC CELLULOSE ETHERS AND ANIONIC SURFACTANTS

This is a continuation-in-part of Ser. No. 592,570, filed Mar. 26, 1984 now U.S. Pat. No. 4,795,327.

BACKGROUND OF THE INVENTION

1. Field of Invention

This invention relates to a carrier base material to be combined with a therapeutically active medicament and formed into a solid, shaped unit dosage form having a controlled and prolonged incremental release of the medicament upon administration. Specifically, this invention relates to a mixture of a water-soluble nonionic cellulose ether and an anionic surface active agent which is suitable for use in controlled release therapeutic compositions.

2. Description of the Prior Art

Water-soluble nonionic cellulose ethers have been used as binders, matrices or carrier bases in sustained release solid dosage forms containing active medicaments, accompanied by lubricants and excipient fillers, as needed. Methylcellulose and hydroxypropylmethylcellulose, particularly the latter, are among the nonionic cellulose ethers which have been most widely used in this manner.

The cellulose ethers are commercially available in various grades under several trade names. The grades available under a given trade name represent differences in composition and molecular weight. Thus, water-soluble methylcellulose (Methocel A, previously designated as Methocel MC, from The Dow Chemical Co., U.S.A. and Metolose SM from Shin-Etsu, Ltd., Japan) has a methoxyl content of 27.5-31.5 weight-% and is available in various viscosity grades. Hydroxypropylmethylcellulose is actually a series of compounds (Methocel E, F, J and K, all previously designated as versions of Methocel HG, from The Dow Chemical Co., U.S.A., and Metolose SH from Shin-Etsu, Ltd. Japan), which of each has a different chemical composition with a methoxyl content within the range of 16.5 to 30 weight-%, a hydroxypropoxyl content within the range of 4 to 32 weight-% and each of which is available in various viscosity grades.

Commercial designations of the various cellulose ethers are based on the viscosities of 2% aqueous solutions at 20° C. The viscosities range from 5 cps to 100,000 cps and represent number average molecular weights ranging from below 10,000 to over 150,000, as calculated from the data in "Handbook of Methocel Cellulose Ether Products" (The Dow Chemical Co., 1974).

Christenson and Dale (U.S. Pat. No. 3,065,143) and Huber, Dale and Christenson (J. Pharm. Sci., 55, 974 (1966) disclosed the preparation of a sustained release drug tablet wherein a high viscosity grade, i.e. high molecular weight, hydroxypropylmethylcellulose, was present as binder to the extent of at least one third of the weight of the tablet. The binders included 4000 cps viscosity grade Methocel 60HG, now known as Methocel E4M, having a 28-30 weight-% methoxyl content, a 7.5-12 weight-% hydroxypropoxyl content and a number average molecular weight of 93,000, as well as 4000 cps and 15,000 cps viscosity grades Methocel 90HG, now known as Methocel K4M and Methocel K15M, respectively, having a 19-24 weight-% methoxyl content, a 4-12 weight-% hydroxypropoxyl content and number average molecular weights of 89,000 and 124,000, respectively.

Christenson and coworkers proposed that water was rapidly absorbed and formed a gel barrier on the surface of the tablet. Drug release was controlled by drug diffusion from and attrition of the gel barrier.

Christenson and Huber (U.S. Pat. No. 3,590,117) reported that neither low viscosity grade hydroxypropylmethylcellulose nor high viscosity grade, i.e. 15,000 cps, hydroxypropylmethylcellulose made acceptable long-lasting troches.

Lapidus (Dissertation, Rutgers State University, 1967) and Lapidus and Lordi (J. Pharm. Sci., 55, 840 (1966); 57, 1292 (1968) studied the use of high viscosity grade methylcellulose (4000 cps viscosity grade Methocel MC now designated as Methocel A4M) and/or low and high viscosity grade hydroxypropylmethycellulose (25 cps and 15,000 cps viscosity grade Methocel 90HG now designated as Methocel K25 and Methocel K15M, respectively) in compressed pharmaceutical tablets and confirmed the proposal of Christenson et al. that drug diffusion and attrition of the hydrated layer determined the rate of drug release.

Salomon, Doelker and Buri (Pharm. Acta Helv., 54 (3), 82 (1979) disclosed the use of 15,000 cps viscosity grade Methocel 90HG (now designated as Methocel K15M) in a tablet containing potassium chloride.

Sheth and Tossounian (U.S. Pat. Nos. 4,126,672; 4,140,755; 4,167,558) disclosed solid dosage forms containing 4000 cps viscosity grade methylcellulose or hydroxypropylmethylcellulose in combination with various additives including gas-generating compounds, e.g. calcium carbonate, and inert fatty materials, so as to by hydrodynamically balanced so that they have a bulk density of less than one in contact with gastric fluid.

Schor, Nigalaye and Gaylord (U.S. Pat. No. 4,389,393) disclosed sustained release solid unit dosage forms in which the carrier base material constituted less than one third of the weight of the dosage form and consisted of hydroxypropylmethylcellulose of at least 4000 cps viscosity grade, having a methoxyl content of 16-24 weight-%, a hydroxypropoxyl content of 4-32 weight-% and a number average molecular weight of at least 50,000, i.e. Methocel J and Methocel K or Metolose 90SH.

The use of high viscosity grades of methylcellulose Methocel A and hydroxypropylmethylcellulose Methocel E, Methocel F and Methocel K, in sustained release solid drug dosage forms is also described in a technical bulletin "Formulating Sustained Release Pharmaceutical Products with Methocel" (The Dow Chemical Co., 1982).

The cited prior art discloses that high viscosity grades of hydroxypropylmethylcellulose of various chemical compositions are useful in the preparation of sustained release solid drug dosage forms. However, Schor, Nigalaye and Gaylord (U.S. Pat. No. 4,369,172) disclosed that effective prolonged release therapeutic compositions were prepared by using as a carrier base material, a low viscosity grade hydroxypropylmethylcellulose having a hydroxypropoxyl content of 9-12 weight-% and a number of average molecular weight of less than 50,000.

Lowey and Stafford (U.S. Pat. No. 3,870,790) and Schor (U.S. Pat. No. 4,226,849) disclosed that effective sustained release tablets were produced by using as carrier base material, a modified low viscosity grade hydroxypropylmethylcellulose having a hydroxypropoxyl content of less than 9 weight-% and a number average molecular weight of 23,000, e.g. Methocel E50. The modification was carried out by exposure of the low molecular weight hydroxypropylmethylcellulose to high humidity or moisture and drying in air, resulting in an increase in the carboxyl content of the polymer.

Lowey (U.S. Pat. No. 4,259,314) disclosed the use of a mixture of hydroxypropylmethylcellulose having a viscosity in the range of 50 to 4000 cps, and hydroxypropylcellulose in the preparation of a controlled release pharmaceutical composition.

The present invention is directed toward further improvements in carrier base materials containing nonionic cellulose ethers for use in the preparation of prolonged release solid pharmaceutical unit dosage forms. These improvements result from the presence of an anionic surfactant.

The addition of 1% of some anionic salts of alkyl sulfates, alkyl sulfonates or alkylaryl sulfonates to 1% aqueous solutions of methylcellulose (Methocel A) or hydroxypropylmethylcelluloses (Methocel E, Methocel F and Methocel K) results in an increase in the viscosity of the cellulose ether solution ("Handbook on Methocel Cellulose Ether Products", The Dow Chemical Co., 1975).

An increase in the rate of solution of a drug results from the presence of anionic surfactants, such as dioctyl sodium sulfosuccinate and/or sodium lauryl sulfate, in the dissolution medium or incorporated into compressed drug tablets, containing water-insoluble binders, including polyethylene (Desai et al., J. Pharm. Sci., 54, 1459 (1965); 55, 1224, 1230 (1966), polyvinyl chloride (Desai et al., J. Pharm. Sci., 55, 1235 (1966) and wax (Dakkuri et al., J Pharm. Sci., 67, 354 (1978); Chambliss, J. Pharm. Sci., 70, 1248 (1981). The presence of sodium lauryl sulfate in a quinine sulfate tablet containing a polyamide binder, decreased the rate of solution of the drug at ph 1.5 but had little effect at pH 7.5 (Choulis et al., Pharmazie, 30, 233 (1975).

SUMMARY OF THE INVENTION

An object of the present invention is to provide a carrier base material for use in the preparation of orally, bucally, sublingually, etc., administered lozenges and tablets, as well as suppositories and other solid unit dosage forms which have a controlled and prolonged release pattern for a systemically absorbable medicament or active ingredient incorporated therein.

Another object of the present invention is to provide a carrier base material which retards the rapid initial release of the active medicament from solid dosage forms containing water-soluble nonionic cellulose ethers.

A further object of the present invention is to provide a carrier base material having a more prolonged release pattern of the active medicament from water-soluble nonionic cellulose ethers.

It has now been found that these improvements in a carrier base material can be achieved by admixture of an anionic surfactant and a high viscosity grade water-soluble nonionic cellulose ether.

DETAILED DESCRIPTION OF THE INVENTION

According to the present invention, it has now been found that important advantages and improvements over prior art products containing water-soluble nonionic cellulose ethers as carrier base materials can be obtained by admixture of an anionic surfactant with a high viscosity grade nonionic cellulose ether.

The nonionic cellulose ethers which are effective in the present invention include, but are not limited to, commercially available, high viscosity grades of methylcellulose, including 1500 and 4000 cps viscosity grades of Methocel A and Metolose SM, as well as high viscosity grades of hydroxypropylmethylcellulose, including the 4000 cps viscosity grades of Methocel E and Metolose 60SH, the 4000 cps viscosity of Methocel F and Metolose 65SH, the 5,000, 12,000, 20,000 and 75,000 cps viscosity grades of Methocel J and the 4000, 15,000 and 100,000 cps viscosity grades of Methocel K and the 4000, 15,000 and 39,000 cps viscosity grades of Metolose 90SH.

The use of high viscosity grades of one or more nonionic cellulose ethers as the carrier base material in a solid unit dosage form, has been disclosed in U.S. Pat. Nos. 3,065,143, 4,389,393, etc., and various articles (loc. cit.). Although these solid dosage forms, e.g. tablets, are characterized by prolonged or sustained release of the active medicament, frequently the release of the medicament during the initial period after the administration of the dosage form, is significantly more rapid than in subsequent periods. This rapid release represents a dumping of the medicament into the gastrointestinal tract, particularly when the carrier is present in low concentrations. This results in an excessive initial concentration of medicament and also reduces the amount of medicament available for release during subsequent periods, i.e. it shortens the total release time.

It has surprisingly been found that controlled release, with a decreased tendency for dumping of the active medicament during the initial release period, as well as prolonged release may be obtained from solid dosage forms in which the carrier base consists of a mixture of an anionic surfactant and a water-soluble nonionic cellulose ether such as methylcellulose or hydroxypropylmethylcellulose, having a number average molecular weight of at least 50,000.

The anionic surfactants which are effective in the present invention include alkali metal sulfates of linear and branched alcohols, e.g. $C_8$ to $C_{24}$ alcohols, and ethoxylated compounds including ethoxylated alcohols, ethoxylated alkylphenols, ethoxylated acids, ethoxylated amides, oils, fatty esters, etc., alkali metal salts of sulfonates of aliphatic and aromatic hydrocarbons including naphthalene, alkylnaphthalenes, naphthalene condensates, alkyl-substituted benzenes, diphenyl derivatives, $\alpha$-olefins, petroleum oils, fatty acids, etc., as well as the alkali metal salts of sulfonates of succinic esters including dialkyl sulfosuccinates.

Representative anionic surfactants include sodium or potassium dodecyl sulfate, sodium octadecyl sulfate, sodium sulfated castor oil, sodium dodecylbenzene sulfonate, sodium linear alkylate sulfonate, sodium sulfonated mineral oil, sodium petroleum sulfonate, sodium salt of naphthalenesulfonic acid-formaldehyde condensate, dioctyl sodium sulfosuccinate and the like.

The weight ratio of anionic surfactant to nonionic cellulose ether in the solid dosage forms may be from 0.005/1 to 3/1. The solid dosage forms may contain from 5 to 95 weight-% of the nonionic cellulose ether.

The nonionic cellulose ethers of the present invention may be used with or without prior humidification or similar treatment and when mixed with the anionic surfactant and an active medicament, the mixture has excellent compressibility and the tablets prepared therefrom are hard and dense, have low friability and provide controlled and prolonged release over an extended period.

Solid drug forms containing the mixture of anionic surfactant and nonionic cellulose ether of the present invention are stable and the release rate does not change over an extended period of storage.

A nonionic cellulose ether having a number average molecular weight of at least 50,000 can be used as the sole cellulose ether, in admixture with an anionic surfactant, in the carrier base material or can be used in admixture in all proportions with other nonionic cellulose ethers having the same or different structure, with a number average molecular weight of at least 50,000.

A nonionic cellulose ether of the present invention can be optionally mixed with about 0 to 30% by weight of the mixture of a cellulose ether with the same or different structure and a number average molecular weight below 50,000 or sodium carboxymethylcellulose or other cellulose ether.

The active ingredient can be of any type of medication which acts locally in the mouth or systemically, which in the case of the latter, can be administered orally to transmit the active medicament into the gastrointestinal tract and into the blood, fluids and tissues of the body without excessive peak concentrations occurring. Alternatively, the active ingredient can be of any type of medication which acts through the buccal tissues of the mouth to transmit the active ingredient directly into the blood stream thus avoiding first pass liver metabolism and by-passing the gastric and intestinal fluids which have an adverse inactivating or destructive action on many active ingredients unless they are especially protected against such fluids as by means of an enteric coating or the like. The active medicament can also be of a type of medication which can be transmitted into the blood circulation through the rectal tissues. Thus, the invention is applicable to sublingual lozenges, buccal tablets, suppositories and compressed tablets. The latter are intended to be swallowed in unit dosage form and upon ingestion according to a prescribed regimen give controlled and slow release of the active medicament, while being protected against inactivating gastric fluids.

Representative active medicaments include antacids, anti-inflammatory substances, coronary vasodilators, cerebral vasodilators, peripheral vasodilators, anti-infectives, psychotropics, antimanics, stimulants, antihistamines, laxatives, decongestants, vitamins, gastrointestinal sedatives, antidiarrheal preparations, anti-anginal drugs, antiarrythmics, anti-hypertensive drugs, vasoconstrictors and migraine treatments, anticoagulants and antithrombotic drugs, analgesics, anti-pyretics, hypnotics, sedatives, anti-emetics, anti-nauseants, anticonvulsants, neuromuscular drugs, hyper- and hypoglycaemic agents, thyroid and antithyroid preparations, diuretics, antispasmodics, uterine relaxants, mineral and nutritional additives, antiobesity drugs, anabolic drugs, erythropoietic drugs, antiasthmatics, expectorants, cough suppressants, mucolytics, antiuricemic drugs, and other drugs or substances acting locally in the mouth, such as topical analgesics, local anaesthetics, etc.

The mixture of anionic surfactant and nonionic cellulose ether having a number average molecular weight of at least 50,000, forms what is called a long-acting, slow dissolving carrier of such a nature that it has a protective, demulcent and buffering effect in the body and causes the active medicament to exert its optimum therapeutic action immediately and incrementally for an extended period of time, so that full therapeutic advantage can be taken of the entire or substantially the entire amount of active medicament administered. This unexpectedly high degree of efficiency is a particular advantage of the invention and minimizes the side effects of the medication.

In making up tablets containing an orally administrable systemically absorbable active component such as one of the heretofore mentioned medicaments, the nonionic cellulose ether and the anionic surfactant are thoroughly intermixed with the medicament which is in powdered or granular form or in solution, and any other needed ingredients which are conventional in tablet making such as magnesium stearate, stearic acid, lactose, starch, fumed silica, hydrogenated vegetable oil and, in general, binders, fillers, disintegrating agents and the like. The nonionic cellulose ether and the surfactant may be mixed in water, alcohol or other media known in the art, and dried to produce granules before intermixing with the medicament and other ingredients. Alternatively, the medicament may be granulated with nonionic cellulose ether and surfactant before intermixing with the other ingredients.

The complete mixture, in an amount sufficient to make a uniform batch of tablets, e.g. 50,000, of which each contains an effective amount of active medicament, is then subjected to tabletting in conventional tabletting machines at compression pressures of 140 to 1125 kg/sq. cm. and, because of the use of the specific carrier material of this invention in the production of the tablets, a product is obtained which has the desired hardness, low level of friability and a predetermined controlled and prolonged action and a regular delayed release pattern so that the medicament is available over a period of 0.25-36 hours, depending on the precise tablet size, hardness and the particular carrier composition. In this way, it is possible to produce controlled and slow continuous release tablets in relatively simple and economical manner on a commercial scale as contrasted with the more elaborate and more complex materials and procedures heretofore employed or proposed.

The moisture content of the carrier used in the preparation of the controlled release tablets may be in the 0.1–10% range, the lower end of the range being preferable when moisture sensitive medicaments are used. If the moisture content is outside of this range, it may be brought within the range by the use of ambient or hot, dry or wet air, using appropriate equipment including static, convection, forced air or vacuum chambers or other equipment well known to those skilled in the art. The moisture content of the carrier during tabletting influences the integrity of the tablet obtained under a given compression pressure. However, the moisture content has less influence on the controlled release characteristics than the composition of the carrier and its concentration.

The release pattern of active medicament from the carrier of the present invention can be controlled according to the particular medication and its intended therapeutic effect. For a sublingual lozenge or tablet, the release pattern may be varied from 0.25 to 4 hours. For buccal tablets, the release period may be 0.25 to 24 hours. For orally administered tablets, the release time may be 2–4 hours, 4–8 hours, 8–10 hours, 10–12 hours, 15–18 hours, 20–24 hours, etc., as desired. For vaginal and rectal suppositories, the release pattern ranges from 2 to 36 hours and can be more or less where indicated. Predetermined release patterns of unusually reliable characteristics can be secured. The invention is of very versatile and adaptable nature giving it a wide range of application and end use.

The following illustrative embodiments of the disclosures of the present invention are non-limiting and variations will be obvious to those skilled in the art.

EXAMPLES 1-2

Controlled release ascorbic acid tablets were prepared from 90% granulation ascorbic acid (90% ascorbic acid, 9% lactose and 1% food starch) and 50 cps viscosity grade hydroxypropylmethylcellulose (Methocel E50 having a 28-30 weight-% methoxyl content, a 7.5-12 weight-% hydroxypropoxyl content and a number average molecular weight of 23,000). The tablets were prepared in the absence and in the presence of granular dioctyl sodium sulfosuccinate (DSS granular—USP containing 85% DSS and 15% sodium benzoate).

The 576 mg ascorbic acid tablets were prepared from the following ingredients:

|  | Example No. | |
| --- | --- | --- |
|  | 1 | 2 |
| Ingredients | mg/tablet | mg/tablet |
| 1. Ascorbic acid (90% granulation) | 640 | 640 |
| 2. Hydroxypropylmethylcellulose (Methocel E50) | 50 | 50 |
| 3. Hydrogenated vegetable oil (Lubritab) | 10 | 10 |
| 4. Dioctyl sodium sulfosuccinate (DSS granular - USP) | 0 | 50 |

Ingredients 1 and 2 were mixed, ingredient 3 was added to the blend and, after mixing, was followed by ingredient 4. The mixture was blended for 20 minutes and then subjected to compression in a Parr pellet press using a 12.7 mm die. The hardness of the tablets was determined on a Pennwalt Stokes hardness tester.

The release rate was determined by using the rotating basket dissolution apparatus described in USP XX, page 959. The basket was rotated at a speed of 100 rpm. The dissolution medium was deaerated distilled water through which nitrogen was bubbled throughout the test period to prevent oxidation of the ascorbic acid released into the medium. The medium was maintained at 37° C. The concentration of ascorbic acid released into the pH 7 aqueous dissolution medium was determined iodometrically in accordance with the USP procedure.

The 576 mg ascorbic acid tablets had the following properties:

|  | Example No. | | | |
| --- | --- | --- | --- | --- |
|  | 1 | | 2 | |
| DSS | Absent | | Present | |
| Weight, mg | 700 | | 750 | |
| Thickness, mm | 4.3 | | 4.5 | |
| Hardness, kg | 4.0 | | 5.0 | |
| Release rate Hour | % | Cumulative % | % | Cumulative % |
| 1 | 76.8 | 76.8 | 53.2 | 53.2 |
| 2 | 14.2 | 91.0 | 34.4 | 87.6 |
| 3 | 9.0 | 100.0 | 9.7 | 97.3 |

The presence of the dioctyl sodium sulfosuccinate clearly decreased the amount of ascorbic acid dumped during the first hour, but had little effect on prolonging the release time.

EXAMPLES 3-4

Controlled release ascorbic acid tablets were prepared from a 90/10 ascorbic acid/ethyl cellulose granulate and 4000 cps viscosity grade hydroxypropylmethylcellulose (Methocel E4M having a 28-30 weight-% methoxyl content, a 7.5-12 weight-% hydroxypropoxyl content and a number average molecular weight of 93,000). The tablets were prepared in the absence and in the presence of the sodium salt of a naphthalenesulfonic acid-formaldehyde condensate (Tamol N).

The 612 mg ascorbic acid tablets were prepared from the following ingredients:

|  | Example No. | |
| --- | --- | --- |
|  | 3 | 4 |
| Ingredients | mg/tablet | mg/tablet |
| 1. Ascorbic acid | 612 | 612 |
| 2. Ethyl cellulose | 68 | 68 |
| 3. Hydroxypropylmethylcellulose (Methocel E4M) | 63 | 63 |
| 4. Hydrogenated vegetable oil | 7 | 7 |
| 5. Sodium salt of naphthalenesulfonic acid-formaldehyde condensate (Tamol N) | 0 | 7 |

Ingredients 1 and 2 were granulated in 95% aqueous isopropanol. The granulate and ingredient 3 were mixed, ingredient 4 was added to the blend and, after mixing, was followed by ingredient 5. The mixture was blended for 20 minutes and then subjected to compression in a Parr pellet press using a 12.7 mm die.

The release rate was determined by using the rotating basket dissolution apparatus with the basket rotating at 100 rpm. The dissolution medium was a pH 1.5 aqueous HCl solution which was maintained at 37° C.

The 612 mg ascorbic acid tablets had the following properties:

|  | Example No. | | | |
| --- | --- | --- | --- | --- |
|  | 3 | | 4 | |
| Tamol N | Absent | | Present | |
| Weight, mg | 750 | | 757 | |
| Thickness, mm | 4.5 | | 4.5 | |
| Hardness, kg | 6.0 | | 6.0 | |
| Release rate Hour | % | Cumulative % | % | Cumulative % |
| 1 | 95.3 | 95.3 | 55.6 | 55.6 |
| 2 | 2.1 | 97.4 | 22.7 | 78.3 |
| 3 | — | — | 11.1 | 89.4 |
| 4 | — | — | 5.5 | 94.9 |
| 5 | — | — | 2.1 | 97.4 |

The presence of the sodium salt of the naphthalenesulfonic acid-formaldehyde condensate resulted in a greatly reduced initial rate of release of ascorbic acid. Further, while the tablet containing the surfactant remained intact after 5 hours, when essentially of the medicament had already been released, the tablet containing no surfactant disintegrated within 2 hours.

EXAMPLES 5-6

Controlled release hematinic ferrous sulfate tablets were prepared from anhydrous ferrous sulfate and 4000 cps viscosity grade hydroxypropylmethylcellulose (Methocel E4M). The tablets werre prepared in the absence and in the presence of sodium dodecyl sulfate (SDS).

The 250 mg ferrous sulfate tablets were prepared from the following ingredients:

|  | Example No. | |
| --- | --- | --- |
|  | 5 | 6 |
| Ingredients | mg/tablet | mg/tablet |
| 1. Ferrous sulfate, anhydrous | 250 | 250 |
| 2. Hydroxypropylmethylcellulose (Methocel E4M) | 200 | 200 |
| 3. Hydrogenated vegetable oil | 5 | 5 |
| 4. Sodium dodecyl sulfate (99%) (SDS) | 0 | 12.5 |

The ingredients were mixed in the same manner as in Examples 1-2. The mixture was subjected to compression in a Parr pellet press using a 9.525 mm die.

The release rate was determined by using the rotating basket dissolution apparatus with the basket rotating at 100 rpm. The dissolution medium was a pH 1.5 aqueous HCl solution which was maintained at 37° C.

The 250 mg ferrous sulfate tablets had the following properties:

|  | Example No. | |  |
| --- | --- | --- | --- |
|  | 5 | | 6 |
| SDS | Absent | | Present |
| Weight, mg | 455 | | 467.5 |
| Thickness, mm | 4.2 | | 4.1 |
| Hardness, kg | 9.0 | | 8.5 |
| Release rate | | Cumulative | | Cumulative |
| Hour | % | % | % | % |
| 1 | 48.5 | 48.5 | 42.0 | 42.0 |
| 2 | 20.8 | 69.3 | 20.1 | 62.1 |
| 3 | 34.1 | 103.4 | 12.0 | 74.1 |
| 4 | — | — | 12.0 | 86.1 |
| 5 | — | — | 13.5 | 99.6 |
| 6 | — | — | 2.7 | 102.3 |

The tablet containing no surfactant disintegrated in the third hour while the surfactant-containing tablet was still essentially intact although deformed after the sixth hour.

EXAMPLES 7-8

Controlled release hematinic tablets were prepared from anhydrous ferrous sulfate and 4000 cps viscosity grade hydroxypropylmethylcellulose (Methocel E4M). The tablets were prepared in the absence and in the presence of the sodium salt of naphthalenesulfonic acid-formaldehyde condensate (Tamol N).

The 250 mg ferrous sulfate tablets were prepared from the following ingredients:

|  | Example No. | |
| --- | --- | --- |
|  | 7 | 8 |
| Ingredients | mg/tablet | mg/tablet |
| 1. Ferrous sulfate, anhydrous | 250 | 250 |
| 2. Hydroxypropylmethylcellulose (Methocel E4M) | 225 | 225 |
| 3. Hydrogenated vegetable oil | 5 | 5 |
| 4. Sodium salt of naphthalenesulfonic acid-formaldehyde condensate (Tamol N) | 0 | 25 |

Ingredients 1 and 2 were mixed, ingredient 3 was added and, after mixing, was followed by ingredient 4. The mixture, after blending for 20 minutes, was subjected to compression in a Parr pellet press using a 9.525 mm die.

The release rate was determined in pH 1.5 aqueous HCl at 37° C. in the same manner as in Examples 5-6.

The 250 mg ferrous sulfate tablets had the following properties:

|  | Example No. | | |
| --- | --- | --- | --- |
|  | 7 | | 8 |
| Tamol N | Absent | | Present |
| Weight, mg | 480 | | 505 |
| Thickness, mm | 4.5 | | 4.8 |
| Hardness, kg | 9.5 | | 9.5 |
| Release rate | | Cumulative | | Cumulative |
| Hour | % | % | % | % |
| 1 | 37.5 | 37.5 | 34.5 | 34.5 |
| 2 | 13.7 | 51.2 | 16.3 | 50.8 |
| 3 | 43.1 | 94.3 | 25.3 | 76.1 |
| 4 | — | — | 10.6 | 86.7 |
| 5 | — | — | 5.8 | 92.5 |
| 6 | — | — | 4.6 | 97.1 |

EXAMPLES 9-10

Controlled release tablets were prepared from anhydrous ferrous sulfate and 4000 cps viscosity grade methylcellulose (Methocel A4M having a 27.5-31.5 weight-% methoxyl content and a number average molecular weight of 86,000). The tablets were prepared in the absence and in the presence of a sodium linear alkylate sulfonate (Ultrawet 40DS, a 40% aqueous solution).

The 250 mg ferrous sulfate tablets were prepared from the following ingredients:

|  | Example No. | |
| --- | --- | --- |
|  | 9 | 10 |
| Ingredients | mg/tablet | mg/tablet |
| 1. Ferrous sulfate, anhydrous | 250 | 250 |
| 2. Methylcellulose (Methocel A4M) | 210 | 210 |
| 3. Hydrogenated vegetable oil | 5 | 5 |
| 4. Sodium linear alkylate sulfonate (Ultrawet 40DS) | 0 | 40 |

Ingredients 2 and 4 were granulated by mixing the 40% aqueous solution of ingredient 4 with ingredient 2 and drying. The granulate or ingredient 2 and ingredient 1 were mixed, ingredient 3 was added to the blend and, after mixing for 20 minutes, the mixture was subjected to compression in a Parr pellet press using a 9.525 mm die.

The release rate was determined in pH 1.5 aqueous HCl at 37° C. in the same manner as in Examples 5-6.

The 250 mg ferrous sulfate tablets had the following properties:

|  | Example No. | |
|---|---|---|
|  | 9 | 10 |
| Ultrawet 40DS | Absent | Present |
| Weight, mg | 465 | 481 |
| Thickness, mm | 4.8 | 4.3 |
| Hardness, kg | 9.5 | 9.0 |

| Release rate | | Cumulative | | Cumulative |
|---|---|---|---|---|
| Hour | % | % | % | % |
| 1 | 96.0 | 96.0 | 69.5 | 69.5 |
| 2 | — | — | 32.2 | 101.7 |

The tablet containing no surfactant disintegrated in 30 minutes.

EXAMPLES 11-12

Controlled release tablets were prepared from anhydrous ferrous sulfate and 4000 cps viscosity grade hydroxypropylmethylcellulose (Methocel E4M). The tablets were prepared in the absence and in the presence of high purity sodium dodecylbenzenesulfonate (Siponate DS-10).

The 250 mg ferrous sulfate tablets were prepared from the following ingredients:

|  | Example No. | |
|---|---|---|
|  | 11 | 12 |
| Ingredients | mg/tablet | mg/tablet |
| 1. Ferrous sulfate, anhydrous | 250 | 250 |
| 2. Hydroxypropylmethylcellulose (Methocel E4M) | 200 | 200 |
| 3. Hydrogenated vegetable oil | 5 | 5 |
| 4. Sodium dodecylbenzenesulfonate (Siponate DS-10) | 0 | 50 |

Ingredients 2 and 4 were granulated in 95% aqueous isopropanol. The granulate or ingredient 2 and ingredient 1 were mixed and ingredient 3 was added to the blend. After mixing for 20 minutes, the mixture was subjected to compression in a Parr pellet press using a 9.525 mm die.

The release rate was determined in pH 1.5 aqueous HCl in the same manner as in Examples 5-6.

The 250 mg ferrous sulfate tablets had the following properties:

|  | Example No. | |
|---|---|---|
|  | 11 | 12 |
| Siponate DS-10 | Absent | Present |
| Weight, mg | 455 | 505 |
| Thickness, mm | 4.1 | 4.7 |
| Hardness, kg | 10.5 | 10.0 |

| Release rate | | Cumulative | | Cumulative |
|---|---|---|---|---|
| Hour | % | % | % | % |
| 1 | 47.5 | 47.5 | 35.0 | 35.0 |
| 2 | 10.8 | 58.3 | 15.8 | 50.8 |
| 3 | 13.4 | 71.7 | 14.2 | 65.0 |
| 4 | 13.2 | 84.9 | 13.7 | 78.7 |
| 5 | 11.5 | 96.4 | 4.1 | 82.8 |
| 6 | — | — | 13.2 | 96.0 |

EXAMPLES 13-14

Controlled release 300 mg theophylline tablets were prepared from granular anhydrous theophylline and 15,000 cps viscosity grade hydroxypropylmethylcellulose (Methocel K15M having a 19-24 weight-% methoxyl content, a 4-12 weight-% hydroxypropoxyl content and a number average molecular weight of 124,000). The tablets were prepared in the absence and in the presence of granular dioctyl sodium sulfosuccinate (DSS granular—USP containing 85% DSS and 15% sodium benzoate).

The 300 mg theophylline tablets were prepared from the following ingredients:

|  | Example No. | | |
|---|---|---|---|
|  |  | 13 | 14 |
| Ingredients | grams | mg/tablet | mg/tablet |
| 1. Theophylline, anhydrous | 61.2 | 306 | 306 |
| 2. hydroxypropylmethylcellulose (Methocel K15M) | 7.2 | 36 | 36 |
| 3. Dioctyl sodium sulfosuccinate (DSS granular - USP) | 7.2 | 0 | 36 |
| 4. Fumed silica (Cab-O-Sil M-5) | 0.3 | 1.5 | 1.5 |
| 5. Stearic acid | 0.7 | 3.5 | 3.5 |

Ingredients 1 and 2 were mixed, ingredient 3 was added to the blend and, after mixing, was followed by ingredients 4 and 5. The mixture was blended for 20 minutes and then subjected to compression in a tabletting machine having a 13.84×7.62 mm punch, under a compression pressure of 280 kg/sq. cm. to make 200 capsule-shaped tablets bisected on one side.

The release rate was determined in deaerated water at 37° C. and 100 rpm by using the rotating paddle apparatus described in USP XX, page 959.

The 300 mg theophylline tablets had the following properties:

|  | Example No. | |
|---|---|---|
|  | 13 | 14 |
| DSS | Absent | Present |
| Weight, mg | 347 | 383 |

| Release rate | | Cumulative | | Cumulative |
|---|---|---|---|---|
| Hour | % | % | % | % |
| 1 | 27.1 | 27.1 | 17.2 | 17.2 |
| 2 | 18.4 | 45.5 | 13.6 | 30.8 |
| 3 | 20.6 | 66.1 | 16.6 | 47.4 |
| 4 | 17.0 | 83.1 | 23.2 | 70.6 |
| 5 | 10.2 | 93.3 | 17.9 | 88.5 |
| 6 | 7.6 | 100.9 | 8.7 | 97.2 |
| 7 | — | — | 4.6 | 101.8 |

EXAMPLES 15-16

Controlled release 160 mg propranolol tablets were prepared from propranolol hydrochloride and 4000 cps viscosity grade hydroxypropylmethylcellulose (Methocel K4M having a 19-24 weight-% methoxy content, a 4-12 weight-% hydroxypropoxyl content and a number average molecular weight of 89,000). The tablets were prepared in the absence and in the presence of sodium dodecylbenzenesulfonate (SDBS).

The 160 mg propranolol tablets were prepared from the following ingredients:

|  | Example No. | | | |
|---|---|---|---|---|
|  | 15 | | 16 | |
| Ingredients | grams | mg/tablet | grams | mg/tablet |
| 1. Propranolol hydrochloride | 48 | 160 | 12.8 | 160 |
| 2. Hydroxypropylmethylcellulose (Methocel K4M) | 45 | 150 | 12 | 150 |

-continued

| | Example No. | | | |
|---|---|---|---|---|
| | 15 | | 16 | |
| Ingredients | grams | mg/tablet | grams | mg/tablet |
| 3. Sodium dodecylbenzene-sulfonate (SDBS) | 0 | 0 | 4 | 50 |
| 4. Fumed silica (Cab-O-Sil M-5) | 0.5 | 1.5 | 0.12 | 1.5 |
| 5. Stearic acid | 1.1 | 3.5 | 0.28 | 3.5 |

Ingredient 3 was dissolved in 10 ml water and one-third of ingredient 2 was added and mixed to form a paste. The latter was dried at 60° C. for 1 hour and placed in a desiccator overnight. The granulate was ground to pass through a 40 mesh sieve. The granulate was mixed with the remainder of ingredient 2, followed by ingredient 1 and, after mixing, was followed by ingredients 4 and 5. The mixture was blended for 20 minutes and then subjected to compression in a tabletting machine having a 10.32 mm diameter round punch, under a compression pressure of 280 kg/sq. cm., to make 300 round tablets without surfactant and 80 round tablets containing surfactant.

The release rate was determined in deaerated water at 37° C. in the same manner as in Examples 13-14.

The 160 mg propranolol tablets had the following properties:

| | Example No. | | | |
|---|---|---|---|---|
| | 15 | | 16 | |
| SDBS | Absent | | Present | |
| Weight, mg | 315 | | 365 | |
| Release rate | | | | |
| Hour | % | Cumulative % | % | Cumulative % |
| 1 | 13.1 | 13.1 | 11.2 | 11.2 |
| 2 | 15.8 | 28.9 | 8.5 | 19.7 |
| 3 | 12.9 | 41.8 | 7.7 | 27.4 |
| 4 | 10.3 | 52.1 | 5.7 | 33.1 |
| 5 | 13.1 | 65.2 | 6.3 | 39.4 |
| 6 | 9.7 | 74.9 | 3.7 | 43.1 |
| 7 | 6.8 | 81.7 | 4.1 | 47.2 |
| 8 | 7.7 | 89.4 | 5.2 | 52.4 |
| 10 | 9.7 | 99.1 | 12.0 | 64.4 |
| 12 | — | — | 5.4 | 69.8 |
| 14 | — | — | 5.1 | 74.9 |
| 16 | — | — | 5.6 | 80.5 |
| 18 | — | — | 1.2 | 81.7 |

The foregoing is exemplary and illustrative of compositions and products responding to the present invention, but it is to be understood that they are not limitative since many active medicaments of various types can be employed in the new controlled and long-lasting carrier so long as they are absorbable into blood or tissue from the general intestinal tract and other bodily surfaces and areas. The medicaments shown in our U.S. Pat. No. 4,369,172 may be used in the practice of the present invention and are incorporated herein by reference. The invention is also intended to cover other dosage forms or forms for application of controlled release ingredients such as vaginal and rectal suppositories and buccal tablets. Lozenges and compressed tablets particularly act on oral, oropharyngeal, pharyngeal and intestinal regions. The total dosage is governed by usual medical considerations or physician's directions and when sufficiently larges doses of active medicament are incorporated into the unit dosage form, systemic as well as local action is obtained to overcome or control the pathological condition or disorder being treated.

What is claimed is:

1. A therapeutically active solid unit dosage form having a controlled and prolonged release pattern upon administration, comprising a mixture of (1) a high viscosity grade water-soluble nonionic cellulose ether having a number average molecular weight of at least 50,000 and a methoxyl content of 16.5-31.5 weight-% and selected from the group consisting of methylcellulose and hydroxypropylmethylcellulose, (2) an alkali metal sulfonate of aliphatic and aromatic hydrocarbons and succinic esters, and (3) a therapeutically active medicament, wherein the cellulose ether sulfonate weight ratio is 1/0.005 to $\frac{1}{3}$.

2. A composition according to claim 1 wherein the nonionic cellulose ether is methylcellulose.

3. A composition according to claim 1 wherein the nonionic cellulose ether is hydroxypropylmethylcellulose.

4. A composition according to claim 1 wherein the alkali metal sulfonate is a dialkylsulfosuccinate.

5. A method for the preparation of a therapeutically active solid unit dosage form having a controlled and prolonged release pattern upon administration, comprising compressing and shaping a mixture of a therapeutically active medicament, a high viscosity grade water-soluble nonionic cellulose ether having a number average molecular weight of at least 50,000 and a methoxyl content of 16.5-31.5 weight-% and selected from the group consisting of methylcellulose and hydroxypropylmethylcellulose, and an alkali metal sulfonate of aliphatic and aromatic hydrocarbons and succinic esters, and wherein the cellulose ether/sulfonate weight ratio is 1/0.005 to $\frac{1}{3}$.

* * * * *